(12) United States Patent
Budd

(10) Patent No.: US 7,310,143 B2
(45) Date of Patent: Dec. 18, 2007

(54) NIST TRACEABLE AUTOMATED VISUAL INSPECTION SYSTEM FOR AN INSPECTION OF PARTICLES IN SOLUTION

(76) Inventor: Gerald Walter Budd, 36853 Heatherton Dr., Farmington, MI (US) 48335

( * ) Notice: Subject to any disclaimer, the term of this patent is extended or adjusted under 35 U.S.C. 154(b) by 390 days.

(21) Appl. No.: 10/981,801

(22) Filed: Nov. 5, 2004

(65) Prior Publication Data
US 2005/0099625 A1   May 12, 2005

Related U.S. Application Data

(60) Provisional application No. 60/518,699, filed on Nov. 9, 2003.

(51) Int. Cl.
*G01N 15/02* (2006.01)
(52) U.S. Cl. .................. 356/335; 356/427; 356/237.1; 356/240.1
(58) Field of Classification Search ................ 356/335, 356/427, 428, 237.1, 238.1, 240.1; 250/223 B, 250/208.1
See application file for complete search history.

(56) References Cited

U.S. PATENT DOCUMENTS 6,498,645 B1 * 12/2002 Knapp et al. ................ 356/427

2005/0040336 A1 * 2/2005 Akkerman et al. ......... 250/343

* cited by examiner

*Primary Examiner*—Gregory J. Toatley, Jr.
*Assistant Examiner*—Abdullahi Nur

(57) ABSTRACT

A method for the substantially complete detection and measurement of all particles, within a predetermined size, range, contained in an injectable solution comprising the steps of: a) rotation of the container causes substantially all of the particles in the injectable solution in the container to be set in motion; b) uniformly illuminating the background around the container with light; and c) detecting at least one of light scatter, light reflection and light extinction caused by said particles, with detectors having a depth of focus of detection in a specified volume of the container. Wherein the detectors are positioned, relative to the container whereby the optical path and field of view allows the sensor sufficient focus to view substantially all of the bottom interior surface of the container and substantially all of the solution volume within the container. The method and apparatus produces a geometric representation of the particles in the detection region, whereby the size of detected particles can be is accurately adjusted to an actual size by either calculation or by calculated offset to allow accurate measurement of particle dimensions.

15 Claims, 5 Drawing Sheets

Top View of Illumination Block
Thru Section A-A

Section B-B

FIG. 5 　　　FIG. 6 　　　FIG. 7
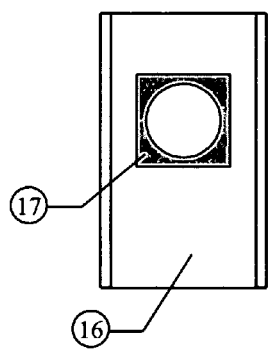
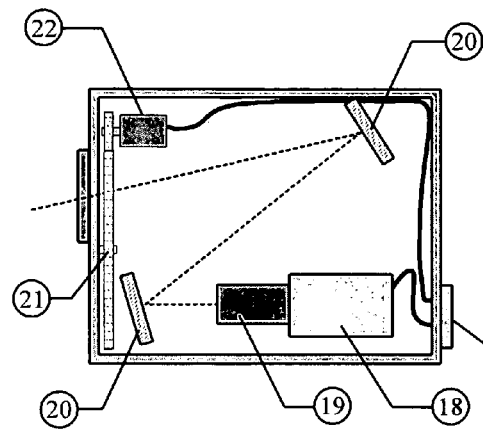
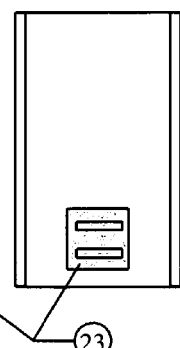
FIG. 8
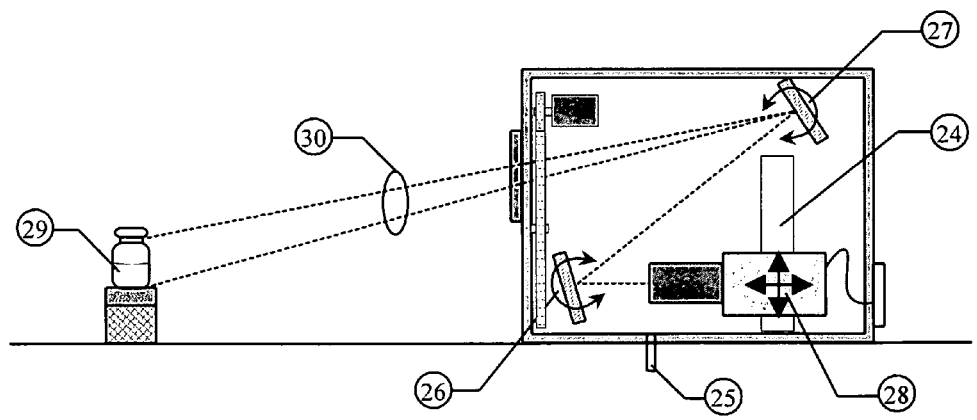

Pixel Count vs. Particle Size (Diameter μm)

NIST TRACEABLE AUTOMATED VISUAL INSPECTION SYSTEM FOR AN INSPECTION OF PARTICLES IN SOLUTION

CROSS-REFERENCE TO RELATED APPLICATIONS

I claim priority to my Provisional Application No. 60/518,699 with filing date Nov. 9, 2003.

FIELD OF THE INVENTION

This invention relates to the procedures and devices utilized in the optical inspection of transparent containers for the presence of contaminating particulate matter and particularly to inspection of injectable pharmaceutical preparations.

BACKGROUND OF THE INVENTION

There is a legal obligation by manufacturers of pharmaceutical injectable solutions to ensure that the product is free of 'visible' particle contaminants prior to their clinical use. This legal obligation can be satisfied by the use of a labor intensive and costly 100% manual inspection of injectable solutions. Less costly automated particle detection systems have been developed. However, in order to satisfy Good Manufacturing Practice, automated inspection systems must be validated prior to any pharmaceutical use. In the validation demonstration, the functioning of the automated system must be shown to be at least as effective in detecting and rejecting containers with 'visible' contaminating particles as the preceding manual inspection.

The performance of human 'visible' particle inspection has been characterized in published reports as a probabilistic process without a sharp particle size accept/reject decision threshold (i.e., a soft decisional process). In the production of an injectable product under good control, the distribution of contaminating particles is approximately hyperbolic, with the concentration of contaminating particles decreasing rapidly as particle size increases. The effect of the 'soft' accept/reject decision threshold is that a proportion of particle-contaminated containers that should be rejected are accepted. A false reject rate of good containers also results from the 'soft' accept/reject decision process. Due to the increased number of containers with particles well below both clinical and control interest, a disproportionate number of the containers that should be accepted are rejected. This disproportionate false reject rate imposes additional costs on the quality assurance program.

Validation of alternative equipment or methods is a Good Manufacturing Practice requirement. The validation of a contaminating particle inspection system is a demonstration that the automated inspection system rejects those containers identified in a manual inspection to be contaminated with "visible" particles. It must show that the rejection capability of the automated system is at least equal to or better than that achieved by the preceding human inspection method. This demonstration must be successfully completed prior to any production use of any proposed automated system.

This demonstration is based on an established statistically evaluated human 'visibility' performance benchmark. To make possible statistical comparisons and evaluations of particle contamination, an inspection model was defined with a statistically described rejection zone boundary. As currently accepted in the pharmaceutical field the Reject Zone includes the group of particle contaminated containers rejected in 70% of a series of manual container inspections. The group of containers with a manual rejection probability equal to or greater than 70% constitute the "must reject" visible particle contaminated group.

Holographic measurements found that the size of the contaminating particles that resulted in the 70% reject rate was 100. mu.m. This determination was made with the particle contaminated containers that were rejected in a 17 second, timed single container inspection performed under 225 foot-candles of illumination, the inspection time is equally divided against a black and white background. The holographic data was correlated with the statistically evaluated probability of detection data to define the minimum 'visible' particle size of 100. mu.m. Accordingly in present practice all containers with 100. mu.m or larger contaminating particles: are considered to be 'must rejects'.

This Reject Zone definition has become a de-facto world standard in validation demonstrations and any proposed automated inspection device must function with at least the capability of the preceding manual inspection. This equivalent functionality is demonstrated by the achievement of an equal or higher rejection rate for the containers identified in the manual inspection to have 'must reject' contaminating particles that are 100 .mu.m or greater.

When current commercially available automated inspection systems were evaluated according to this standard, it was determined that none could demonstrate, in a single inspection, results as secure or as selective as that achieved by human beings. The proportion of "must-reject" containers rejected in a single automated inspection is between half and two thirds that of a skilled human inspector.

As a result, in order to validate these automated inspection systems (to match their inspection security to that of the preceding manual inspection), a two inspection sequence is currently employed. Only containers accepted in both inspections are accepted for stock. Containers rejected in either of the two sequential inspections are eliminated.

It has been determined that the limiting particle rejection/detection probability for an inspection system is the proportion of the liquid contents that have been examined for particulate contamination. A complicating factor is that the position of a contaminating particle in a container at the start of each inspection is completely random. This random initial particle position results in random distribution of particle orbits and velocities within the container. The random particle velocity distribution ranges from zero-to some design maximum.

A defined velocity of particle movement is employed to distinguish between contaminating particles and stationary container markings and optical defects. Particles that do not traverse the fractional inspected volume or that move with insufficient velocity are not detected. To improve the inspection security results, the two-inspection 'game of chance' technique to reduce the effect of the random particle position and velocity is employed. Application of classical probability theory shows that particle detection security is enhanced but the discrimination of the accept/reject decision compared to manual inspection is impaired when this inspection technique is employed. The cost for this improvement in detection probability is a four to six fold increase in the false rejection rate of the manual inspection.

Ideally, secure detection, sizing and identification of the contaminating particulates are an essential part of the control of the production of pharmaceutical injectable products. However, secure detection of randomly occurring and randomly positioned particles in sealed transparent containers requires inspection of the full volume of the container. In addition, accurate particle sizing in the present automated inspection systems requires sharp particle images. However, with present art, the sharp image requirement cannot be achieved for the size range of containers used for pharmaceutical injectable products.

In addition, only a portion of the contents of the container volume is normally inspected for contaminating particles and accordingly the security with which 'must reject' containers are rejected in the partial container volume inspection cannot exceed the proportion of the container volume containing contaminating particles inspected.

U.S. Pat. No. 3,627,423, issued Dec. 14, 1971, discloses an improvement in particle contrast, and thus detectability, that results from the use of narrow aperture lighting of the liquid volume contents of the container. This patent teaches that narrow aperture lighting of the liquid volume contents of the container that transits the glass envelope or the container in a near perpendicular condition minimizes the reduction in particle contrast that occurs when a broad area light source is employed for the inspection. The use of narrow aperture lighting of the liquid volume contents of the container to produce forward scatter lighting also minimizes the reduction of particle signal dynamic range that occurs when glare reflections occur at the meniscus or the container bottom. Glare reflections are produced when a bottom mounted light source parallel to or on the container axis is employed for the inspection. The teachings of this patent indicate that measurements near the meniscus or the bottom of the container are less sensitive.

At present there are two automated inspection methods, U.S. Pat. No. 5,365,343 ('343 patent) issued Nov. 15, 1994, and U.S. Pat. No. 6,498,645 ('645 patent) issued Dec. 24, 2002, by the present inventor that can equal or surpass the two important attributes of the human inspection for contaminating particles in sealed containers (the teachings of this patent are also incorporated herein by reference thereto). These attributes are the reliability of detection of these contaminating 'visible' particles and the selectivity of the human accept/reject inspection characteristic. Both attributes are evaluated with statistical measures derived from the probabilistic analysis of human inspection results.

In the '343 patent, an imaging lens is used at its maximum energy collecting capability and its maximum resolution to achieve maximum particle detection depth. Two light sources are employed, a forward scatter light source is used for small and low contrast particle detection. A second collimated light source, with intensity at the detection, plane ranging from 0.2 to 10%, is used as a back lighting means. The contaminating particles are sized numerically by the peak change, either positive or negative, in light flux collected from the moving particle. This patent teaches that the light flux collected from an image and its blur surround is essentially constant for a controlled displacement around the plane of best focus.

In the '645 patent the measurement approach avoids reliance on sharply defined image edges to detect and size particles, and it results in a total light flux particle measurement. It relies, however, on the presence of uniform illumination level for the inspected container and system measurement stability. This reliance results in particle detection variability determined by the variation in the realizable illumination uniformity of the inspected container and variation of the detection capability of the system. The use of the light flux sizing as described in the '645 patent makes it possible to inspect the full volume of a container up to 30 mm in diameter with a 75 mm focal length lens at maximum aperture of f stop equal to 1.8. The previous detection volume limit was imposed by detection volumes 1 to 3 millimeters thick centered on the axis of the container and extending through its liquid contents. Since the reliability of detecting particles in a container is proportional to the total container volume inspected, inspection reliability for containers up to 30 mm in diameter approaches 100% with the use of the teachings of the '645 patent. Determination of the size of a detected particle is achieved with a stored transfer curve of particle size versus the light flux peak detected. The methodology requires both light source and measurement system stability to maintain the calibrated particle sizing accuracy. Particles are detected by the variation of light level received in each element of the photo detector. Any change in the stability of the light source or the measurement system affects the peak value of the detected light flux due to a particle and thus the particle sizing accuracy. The approach described in the '645 patent sacrifices particle image shapes to achieve secure detection of the particle signal throughout the volume of the container.

The use of the described present invention provides a uniform illumination field within the volume of a container that permits the detection of a contaminating particle in 90% of the solution volume with a single image acquired by a photo detector (CCD Camera). The present invention produces the uniform illumination field using a uniquely shaped light emitting diode (LED) array along with special diffusing element that surrounds the container on at least 3 sides. The methodology produces a background illumination that enhances the detection of contaminating particles and allows the trajectory (position within container) of contaminating particles to be mapped. With the capture of successive images the invention provides nearly 100% detection of contaminating particles contained in the solution. The image processing technique uses a software algorithm to normalization (reduce localized variations) in the image background. The result of the uniform illumination on the image is to minimize variations in the calculated size of the contaminating particles. In addition, the invention provides geometrically correct images of contaminating particles that may be accurately, sized when positioned with specific inspection zones. The size of the contaminating particles are determined by comparison of the pixel dimensions of a particle to the pixel dimensions of previously collected sample container(s) seeded with a single NIST traceable particle. The present invention allows for the generation of standard calibration curve for the determination of actual size of contaminating particle (diameter in µm) verses the apparent particle size (diameter in pixels).

BRIEF SUMMARY OF THE INVENTION

It is an object of the present invention to transform the present probabilistic detection of contaminating particles present in a container, even larger than 30 mm in diameter, into a deterministic detection and accurate measurement process It is a further object of the present invention to provide a method to generate a uniform illumination field within liquid volume in a container to enhance the detection and measurement of contaminating particle(s).

It is a further object of the present invention to provide a method that evaluates the focused or nearly focused image of particle measurement with a direct, physically based particle size evaluation in a defined area.

It is a further object of the present invention to provide a method to acquire image(s) of heavy contaminating particle (s) that are positioned on the bottom of the container.

It is a still further object of the present invention to provide a method that transforms the present random array of particles within a container into a positioned array in a defined portion of the container to be inspected with sufficient spatial resolution for the accurate determination of size and/or shape.

It is yet another object of the present invention to provide a means for the construction of an accurate instrument calibration curve that will correlate actual size of NIST traceable particles to the apparent dimension in the image sensor (pixels)

Generally the present invention comprises an improved method for the substantially complete detection of all particles, within a predetermined size range, contained in an injectable solution, in a transparent container. In preferred embodiments the container has a circular cross section, though some containers may depart from circular symmetry in less preferred embodiments. The method comprises the steps of:

a) pre-positioning particles in the container whereby rotation of the container causes substantially all of the particles in the injectable solution in the container to rotate, with approximately equal initial velocity, in a shell volume adjacent the inner walls of the container, with said shell volume having a predetermined thickness;

b) illuminating all the particles rotating within the shell volume with lighting means;

c) detection of particles by movement on the container bottom and in solution by orienting the sensor with a downward angle with respect to the axis of symmetry of the container;

d) detecting at least one of light scatter, light reflection and light extinguishing caused by said particles, with detector means having a depth of focus of detection in which said particles remain in near-focus within the volume of the container; and e) measuring at least one of light scatter, light reflection and light extinguishing caused by said particles, with detector means having a depth of focus of detection in which said particles remain in focus within the center volume of the container.

wherein the sensed signal is corrected for the asymmetries of the imaging system by correction means either by computation or by repositioning the detector means relative to the container, whereby a focused imaging plane is formed at the container axis and then mechanically or electro-mechanically offset closer to the imaging sensor than the center of the cross section, whereby the size of detected particles in the opposite volumes is accurately mathematically compensatible to an actual size. The lighting means provides a multiplicity of directed light emitting diodes (LED's), mounted on three of the interior walls of a cubic structure with an acrylic element placed in the center. The diffusing element has a "U" shaped channel removed along the centerline of cubic structure in which the container being tested is positioned. The "U" shaped diffusing element is designed to uniformly diffuse the light entering the container. The sample container rest in slightly recessed pocket centered on a rotational device. The center of the axis of rotation is positioned to coincide with the center of radius and width of the "U" shaped channel in the diffusing element. The channel width of the diffusing element should be approximately 1.5 times the diameter of the container being inspected. The lighting means may be adjusted to enhance the image characteristics by activating various LED lighting elements within the structure. Contaminating materials with less optical density can be enhanced in the image by reducing the radiant energy of the illumination system.

With said detector being mounted inside a sealed enclosure the critical optical components of the system can be protected from the environment. The detector is mounted in such a manner so that so that the optical path can be easily adjusted with the target area. The design of the sensor enclosure allows for the insertion of optical filter elements within the optical path of the invention.

These and other objects, features and advantages of the present invention will become more evident from the following discussion and drawings in which:

BRIEF DESCRIPTION OF THE SEVERAL VIEWS OF THE DRAWINGS

FIG. 5 illustrates the front view of sensor enclosure;

FIG. 6 illustrates the interior of the sensor enclosure and relative position of key components;

FIG. 7 illustrates the rear view of the sensor enclosure;

FIG. 8 illustrates the relative position of sensor enclosure with respect to the sample container and spin access of rotational device;

DETAILED DESCRIPTION OF THE INVENTION

The invention is a combination of three key components configured in the proper way to determine the maximum dimension of particles in solution. The key components are an Illumination Module, a Sensor Module, and an Image Processing System with specific software. The invention has offers several unique components that allow the particle to sized accurately. The invention has many uses but is designed primarily for the detection of contamination in clear solutions like those used in the pharmaceutical products.

Figure 1:
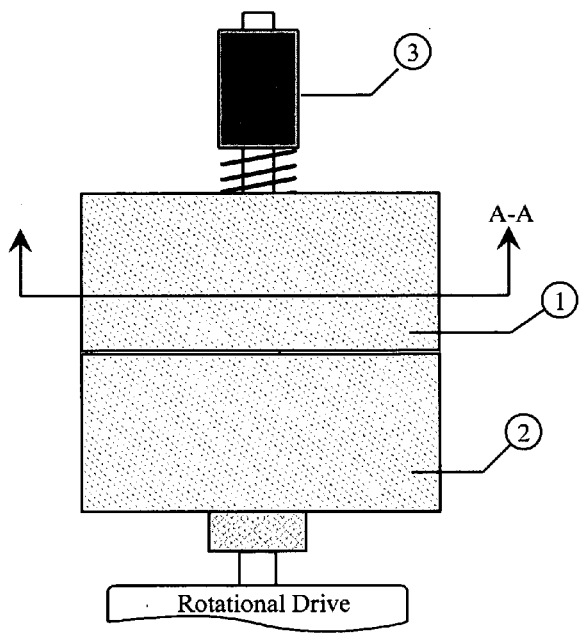
FIG. 1 illustrates the exterior of the Illumination Module as viewed from the side.

The first key component is a unique illumination system designed to provide a very uniform background for the inspection of product in cylindrical vessels such as pharmaceutical vials. The illumination system is cube shaped with a channel slightly larger than the diameter of the vessel removed from the center, hereafter we shall reference to this system as the illumination module. The basic configuration is illustrated in FIG. 1. The cube is constructed using an upper and lower halves indicated by items 1 & 2. The construction is from a solid piece of aluminum that has material removed to hollow its inner. The aluminum is anodized black to insure that no reactive surfaces are on the components. The sample product (pharmaceutical vial with liquid contents) is centered on a recessed puck and held in position by a spring loaded clamping device. Item 3 in the illustration represents the retaining sleeve for spring and alignment shaft.

Figure 2:
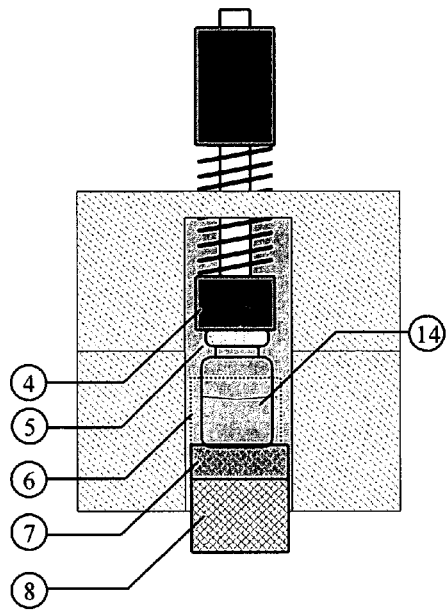
FIG. 2 illustrates the exterior and a portion of the interior of the Illumination Module as viewed from the front or sensor viewing direction.

FIG. 2 illustrates the front view of the illumination cube with the channel exposed. The sample product (item 14) is positioned on a recessed bottom holder (item 7). The cap of the sample product (item 5) is usually constructed of a rubber liner (cap) and a protective aluminum closure. The clamping device used to securely hold the sample container during rotation also has a recessed cup in the contact area to center the sample (item 4). The clamping device incorporates ball bearings to insure that the closure on the sample is not damaged. The recessed bottom holder has two different recessed diameters on the top and bottom surfaces. The recessed holder is held tightly during rotation of the drive mechanism (item 8 and rotational drive of FIG. 1) using three equally spaced pins. The inspection window (item 6) is centered in the most uniform area of the illumination field. The illumination field is made uniform by properly shaping the diffusing media and adjusting the LED lighting sources.

Figure 3:
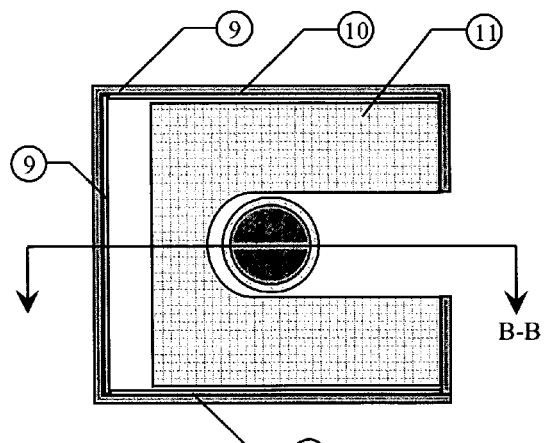
FIG. 3 illustrates cross-section (A-A) of the Illumination Module interior as viewed from above. The section cuts through the sample container to show relative position of container with respect to the illumination diffuser.

FIG. 3 is the top view of the illumination module as seen through section A-A of FIG. 1. The Aluminum housing (item 9) is hollowed out to leave only a thin wall. Placed around the three walls opposite the opening, are flat panels light emitting devices (LED's). The LED flat panels are fabricated with a high density of LED's per unit area, reference Phoenix Imaging 4100 series LED backlights. The LED panels provide a uniform illumination and can be turned on or off as required for the inspection. The uniform illumination field is created using a special design diffusing media, item 11 in FIG. 3. The diffusing media is fabricated from a cube of optical grade polycarbonate or acrylic. As can be seen in the Figure the test sample is placed along the centerline of the illumination module. A cutout shaped like an elongated "U" is made in one side and faces the optical sensor. The cutout is slightly larger than the diameter of recessed bottom holder and test sample. The LED illumination panels can be adjusted for backlight, diffuse sidelight (forward scatter) or a combination of both. A voltage controller allows the output of the LED lighting panels to set for optimum contrast/performance. The front surface of the illumination module, except for the viewing channel, is hidden by the aluminum housing to protect over exposure of the sensor from the LED lighting panels.

Figure 4:
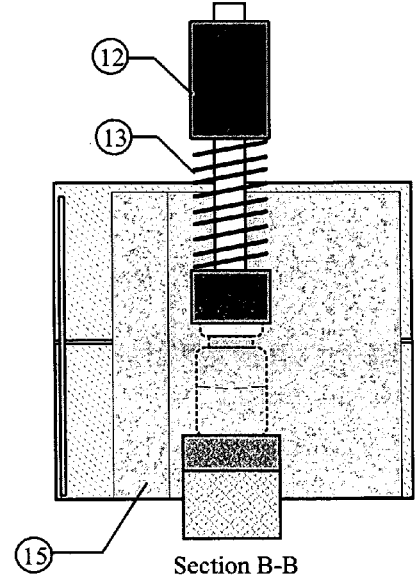
FIG. 4 illustrates cross-section (B-B) of the Illumination Module interior as viewed from the side. The section cuts through the sample container to show relative position of components.

FIG. 4 illustrates the cut away view of the illumination module as seen through section B-B of FIG. 3. The illumination diffuser and LED panels extend below the bottom of the sample vessel to insure uniform lighting across the entire image. This unique design hides the corners of the LED panels and makes the entire illumination field a uniform intensity. Variations in the height of sample container are accommodated in the inspection position with the aid of compliance spring (Item 13) and low friction guide (item 12). Unlike previous designs this system allows particles in the solution to be tracked throughout the entire volume. The technology implements high resolution area scan sensors that acquire full frame images in several milliseconds. The sensor is able to scan the entire volume of the solution each frame. The detection of particles>40 μm are isolated with 100% certainty within the inspection cycle.

The second major component in the inspection system is the Sensor Module. The sensor module is designed as a sealed unit with no user serviceable components. The image sensor, optics, filters are pre-calibrated in known positions in the sensor module. FIG. 5 illustrates the front surface of the sensor module (item 16) and the viewing window (item 17). The viewing window is constructed using a material with anti-reflective coating. The window is sized to accommodate the field of view (FOV) necessary to acquire the image of the sample under inspection.

FIG. 6 illustrates one internal configuration of the Sensor Module. The photosensitive detection system used in the sensor module is either a high-resolution CCD sensor or in some applications a sensitive CMOS sensor may be used. The CCD sensor (item 18) must be of mega-pixel resolution or larger and is located in one corner of the sensor module. The optical system is very important in the detection of small particles in solution. High quality lenses should be used to enhance performance of the inspection (item 19). The optical path length (the distance between the CCD sensor and the sample under inspection) has an effluence of the imaging characteristic and performance of the system. In some cases the path length must be longer than the available distance between the physical location of the CCD sensor and the sample under inspection. In this case, a folded optical path is employed by reflecting an image of the object through one or more mirrors to increase the apparent distance between object and CCD sensor as illustrated by items 20 in FIG. 6. The longer the focal length of the lens the greater the depth of field and therefore the larger the volume that can be inspected. When instrument volume is at a premium the folded optical path allows for better system performance in a small footprint enclosure.

The sensor module incorporates an internal optical filter wheel. The wheel is a disk with one or more filters (polarizing, grayscale attenuation or color) that allow the system to change the CCD sensor characteristics very rapidly. The filter wheel is illustrated as item 21 in FIG. 6. The filter wheel is optional and is not required for every inspection. The filter wheel is driven by a small stepper or servomotor (item 22) from inside the sensor module. The filter wheel may be substituted with a liquid crystal window in grayscale applications and has the benefit of not having a mechanical moving components. The liquid crystal window attenuates the amount of light allowed to pass in the optical path. This ability to attenuate the optical path, whether electronically or mechanically, is critical in the inspection application. The inspection process will be discussed later in this document.

The sensor module is a seal box with all optical devices mounted inside. The sensor connections are made by way of a multi-pin connector on the rear of the module. The multi-pin connector system allows the user to easily replace a defective sensor module with another sensor module that is pre-configured for the application with no user setup required. When the initial application is installed it defines the configuration of the sensor module. This configuration is archived at the plant of manufacture so that an exact duplicate sensor module can be assembled for use as required. On the bottom of the sensor module is a pair of holes designed to accept mating tapered dowel pins (item 25 of FIG. 8). The dowel pins only allow the sensor module to be installed in a specific location in the inspection system. The multi-pin connector is used to connect the sensor and aperture control (liquid crystal window or filter wheel) inside the sensor module without having the user open the enclosure.

The relative position of components with respect to each other is critical for system operation. The locations are defined by each application. Enhancement have been made to the interior of the sensor module to allow each unique configuration to be setup easily and quickly. The CCD sensor is mounted on one or more dovetailed slides that permit the unit to translate in orthogonal directions as indicated by item 28 in FIG. 8. The dowel pins insure that the sensor module is mounted the proper distance from the object under inspection (item 29). The front a surface mirrors used to guide the optical path use goniometer mountings for fine alignment of the field of view to the target position (items 26 & 27). The region of interest (ROI) when inspecting solution filled pharmaceutical vials is from the bottom of the meniscus to the bottom of the vial as illustrated by item 29. The solid angle of the optical path defines the FOV of the image and is determined primarily by the focal length of lens used, identified as item 30. The solid angle of the optical path must be clear of obstructions.

Figure 9:
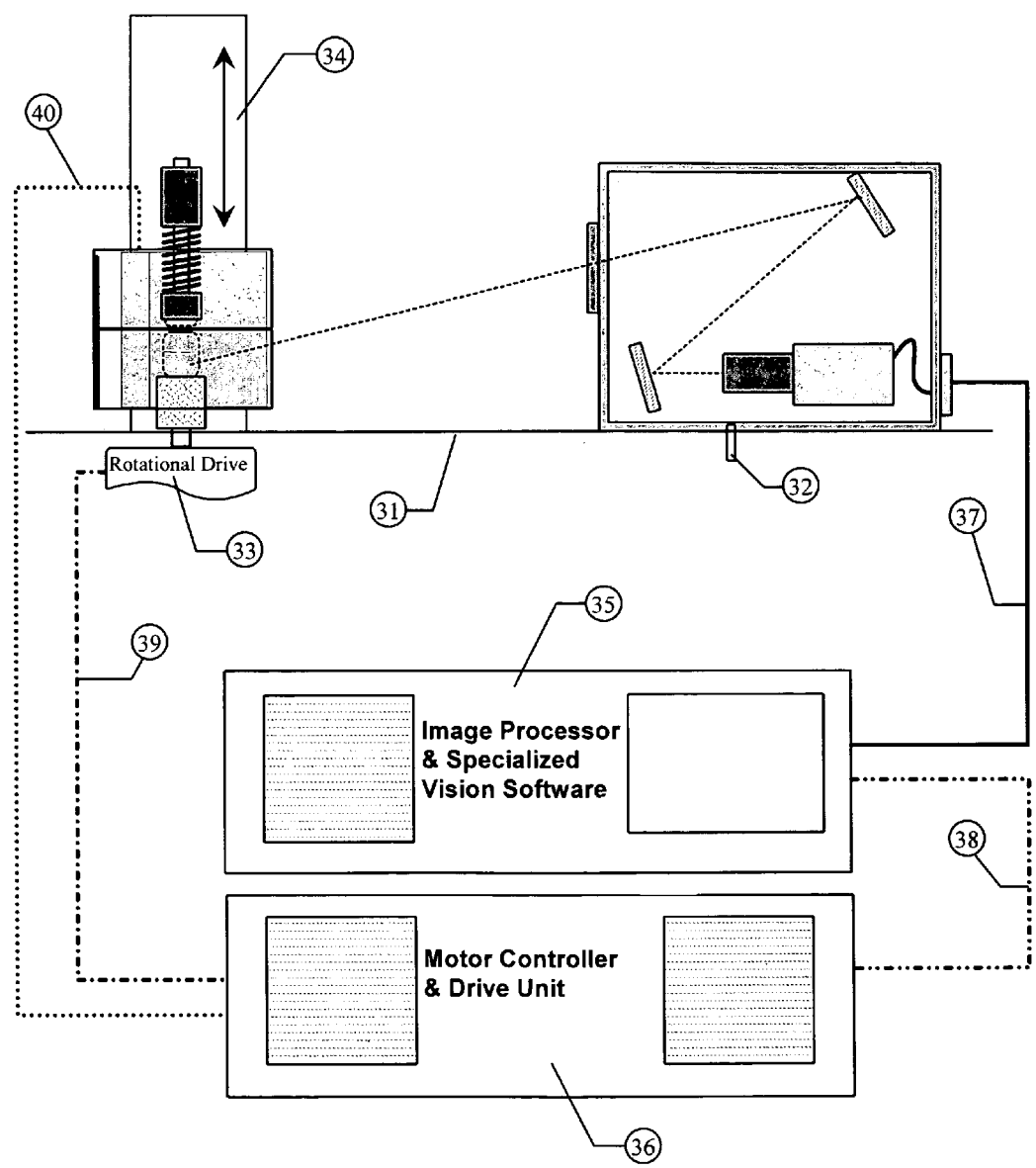
FIG. 9 illustrates the inter connections between the key components of the invention.

FIG. 9 illustrates the complete configuration of a single inspection cell. The key components Illumination and Sensor Modules are mounted on a flat tabletop or work piece. The working distance and angle of viewing of the inspection cell is defined by the distance between the axis of rotation of the rotational drive (item 33) and the dowel pins (item 32). The object height above the work plane (item 31) is defined by the height of the recessed container holder mounted on top of the drive shaft. A word should be said about the rotational drive (item 33). The method of rotation is not as important as the parameters used to perform the function. The best results are achieved with a drive system that is capable of accelerating and decelerating quickly. The physics of the inspection require that the drive system accelerate rapidly, maintain a constant velocity and then decelerate rapidly. The profile of the motion curve is very important and defines the motion or path of the contaminating particle in the solution. The wall of the vessel must couple with the solution within. It is important the acceleration/velocity profile does not cause cavitation (the generation of air bubbles in the solution). If cavitation is the result of the motion profile the sample can not be inspected reliably. The motion profile must move the heavier particles without allowing the meniscus to creep up the walls to the vial neck. If the vial is spun too vigorously the particle may be spun up into the cap of the container and be held there. The correct motion profile of an inspection is defined by the size/shape of the container and the viscosity of the solution inside it. This invention allows the user to study the shape characteristics of the meniscus while defining the motion profile.

The Illumination Module is mounted on a linear translator that allows it to be raised and lowered. Raising the Illumination Module provides clear access to the sample container and rotational drive/recessed holder. The linear translator (item 34) is normally positioned at the rear of the Illumination Module. This has the additional benefit of reducing the spacing between adjacent inspection units if more than one is implemented. The linear translator implementation can be assisted by air (cylinders), electric (or magnetic), or mechanical (lead screws or cams). The linear translator should be parallel to axis of rotation.

The last key component in the inspection system is the Image Processor and Specialized Vision Software. The Sensor Module sends image data (optical picture in electronic format) to the Image Processor (item 35). The image processor acquires high resolution (minimum 1280×1024 pixels) with a minimum signal to noise of 10. bits (1024 grayscale levels). Much higher resolution sensors may be used when cost or cycle times at not as critical. The preferred data transport mechanism is to use the Camera-Link (CL) format indicated as item 37. The analysis of the image data is performed using special software written to extract the particles in solution. The system acquires multiple HR images in rapid secession (4-60 images) and stores them in separate frame buffers. The sensor acquisition control allows the application to define the region of interest (ROI) from within the field of view (FOV). The system should use frame rates (number of full pictures per second) in the range of 24-60 frames per second. If partial frames are used to acquire images with smaller field of view the frame rates increase. The optimum frame rate is one in which the largest diameter particle (assuming spherical object) translates or moves at least one diameter between successive images. It may be the case that the viscosity or fluid motion is slow and a delay must be placed between successive image acquisitions. The software compares each image with the previous image (except in the case of the first) and isolates any object with the image field of view that moves. A more advanced approach is for the software to compare each image to a specified image in the acquisition sequence so that the relative movement of the particle(s) can be very small and still be detectable. This is important when detecting the motion and then sizing of heavy or large particles that tend to settle very rapidly. A special image-processing algorithm is used to extract the moving particles and then determine their relative size.

The Image Processor (item 35) acts as the inspection cell master controller and controls the other modules or devices in the inspection cell. The Motor Controller (item 36) is used to generate the motion profile in conjunction with the rotation drive. The request to perform a motion profile is given to the motor controller over item 38. The control line between the motor controller and the motor is indicated by item 39. In the evaluation unit a high torque stepper motor with lower inertia was used to rotate the test sample. The motor controller also controls turning the various LED lighting panels on or off during the inspection (item 40). When the motion profile has been completed the motor controller reports back to the image processor and the image processor begins acquiring the necessary images. Depending on the number and size of image acquired the entire inspection cycle requires from one to several seconds.

Figure 10:
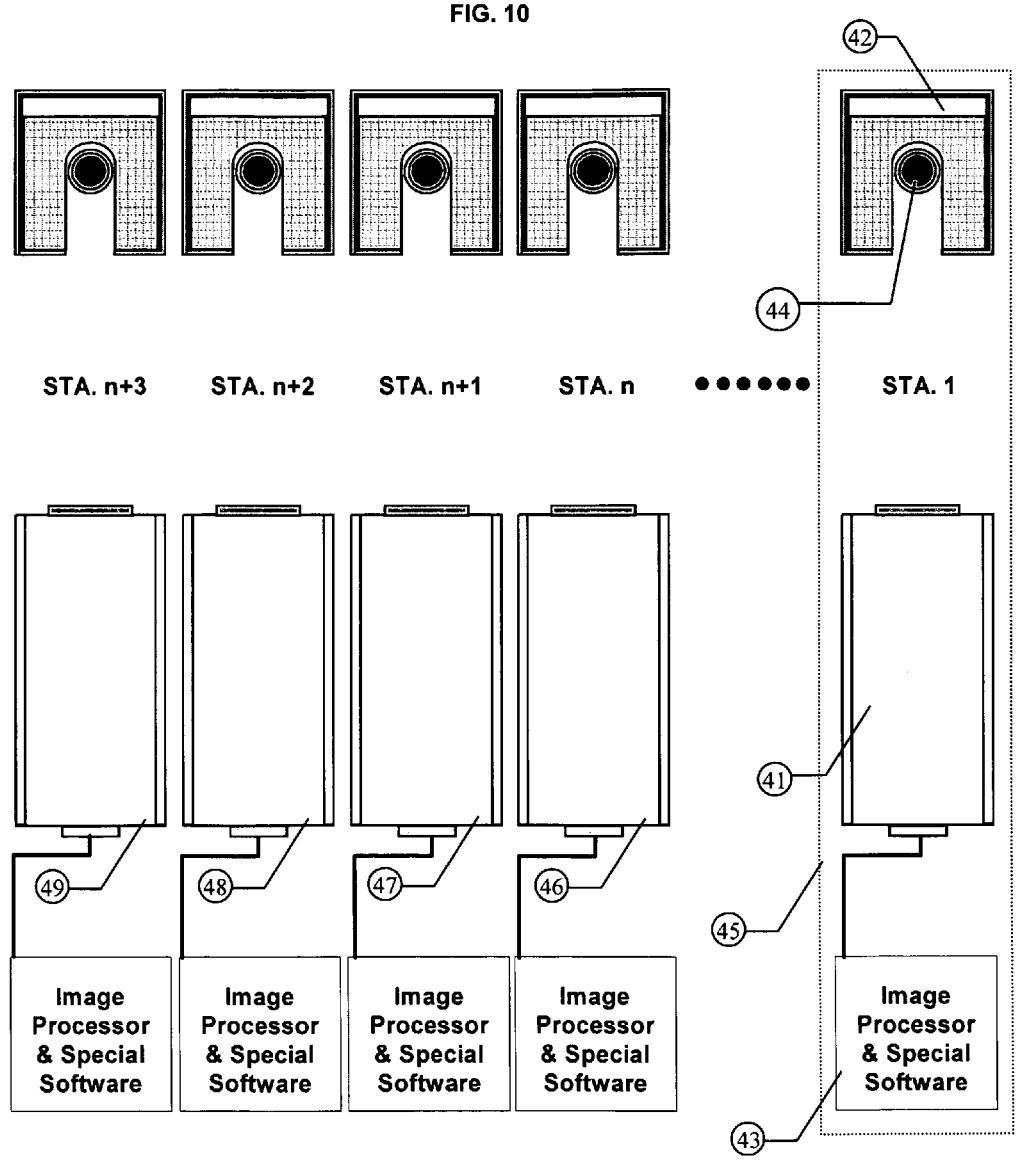
FIG. 10 illustrates a multi station configuration of the invention.
Figure 11:
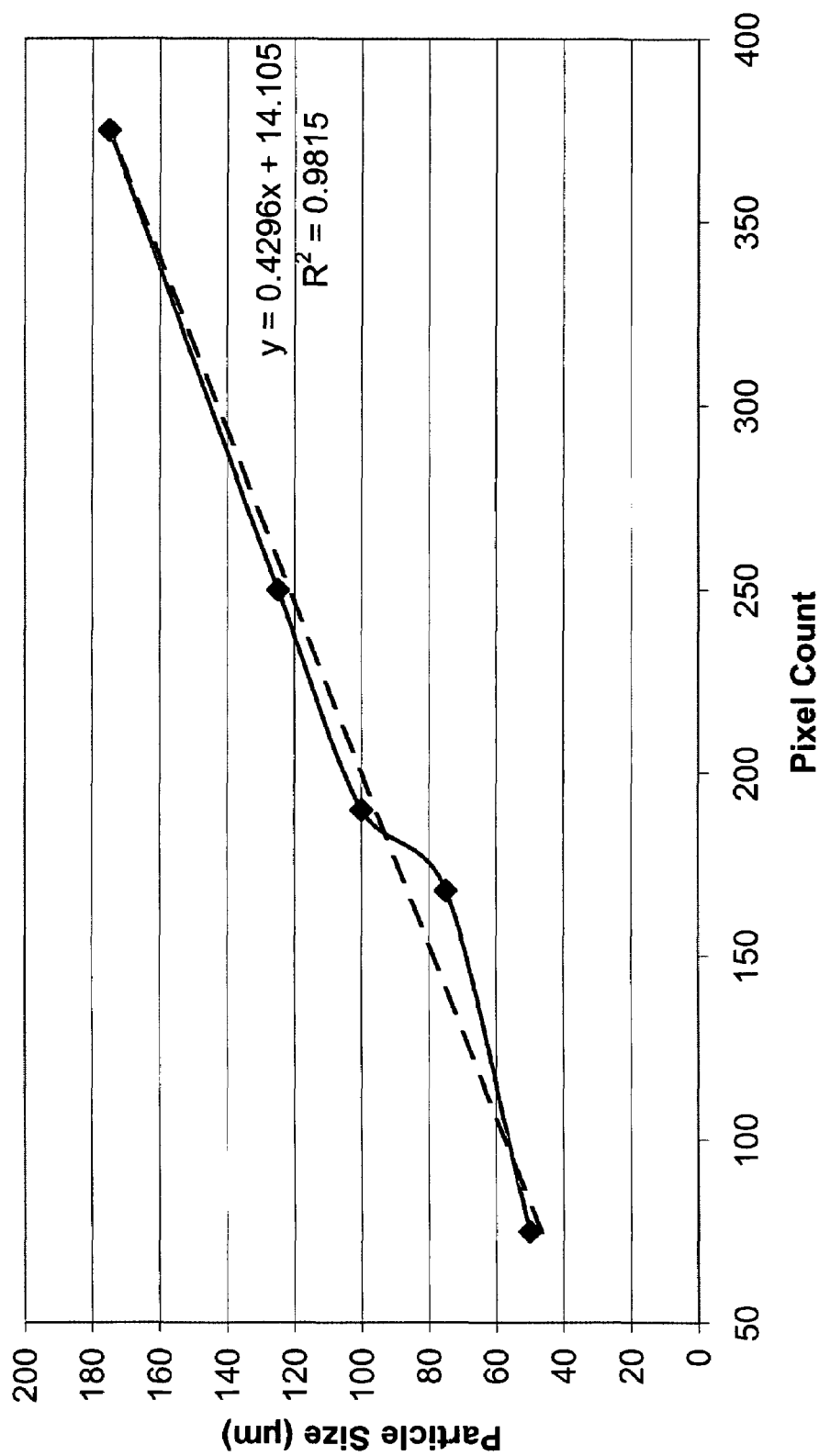
FIG. 11 is a graph showing the linearity of a plot of the apparent size of the particle as determined by the invention plotted against the actual size of NIST traceable single seeded samples.

If the average cycle time is three seconds for a rigorous inspection then the inspection cell is limited to 20 inspections per minute. The Laboratory Assay System is a small single inspection cell unit designed to handle a limited number of samples per hour. This does not lend itself toward mass production inspection. However, the design concept can easily be expanded to incorporate multiple copies of the inspection cell. FIG. 10 illustrate an approach that can handle the desired volume by implementing multiple inspection cells side by side. The inspection cell is indicated as item 45 and is comprised of a Sensor Module (item 41), an Illumination Module (item 42), an Image Processing Module (item 43) and the sample on rotational drive (item 44).

The large volumes of sample product would be moved into the inspection position this may be performed at all stations simultaneously if desired. However simultaneous operation is not necessary as each inspection cell is independent. The simultaneous operation would reduce the cost of the rotational motion by using a common drive mechanism.

If a simultaneous operation were used the steps would include,
 1. Loading of sample into the spin station
 2. Select illumination configuration
 3. Run samples through the motion profile
 4. Acquire necessary images 5. Turn off illumination 6. Start samples unloaded while simultaneously start analysis of images 7. Analyze images for possible particle defects and report findings 8. Flag reject samples containers 9. Repeat sequence as required It would be difficult to hand-load the laboratory assay system at 20 vials per minute. However, if 10 stations were used in a large volume production system it would be easy to achieve 200 samples per minute. The key feature of this inspection technology is the ability to determine the size of particle inspection with an accuracy range of 20 µm when examining a 2-10 ml sample. The user can select an exact cut-off limit below which particles smaller than the limit will be accepted. The product is not rejecting simply on a detection basis but on a particle size basis.

When calibrated using NIST traceable standard samples the inspection system provides a method for validation for maximum dimensional particle sizing. This also provides a more realistic measurement of non-spherical particles like platelets, fibers and non-uniform shapes (glass shards). The Module concept provides NIST traceable inspection not only when shipped but virtually forever. This is possible because of a stable detector with permanent size calibration.

What is claimed is:

1. An improved apparatus for the detection of contaminating particles in the fluid of small containers in which the apparatus produces a uniform illumination field for consistent grayscale detection and measurement of moving particles in the solution using a machine vision measuring system comprising:

a) an image processing computer for image acquisition, image storage and image processing capability;

b) the image processing computer comprising memory for storing the images formed by the camera;

c) the image processing computer also comprising digital parallel input/output digital serial, and Ethernet communication capabilities for providing messages to external devices to report one or more measurements or characteristics of the particles moving in the solution;

d) the image processing computer executing control software stored in a computer readable medium, for allowing request and response signals from external devices indicating a small container to be inspected, for causing the image processing computer to perform image analysis for extraction of the summation of grayscale values of the moving particles in the solution found within the small container, as well as for causing the image processing computer to store a reference images of an acceptable quality of small container with no presence of contamination particles in a memory location referenced by a specific identification code that is unique to a small container size and shape with a specific fluid fill level;

e) an image sensor with appropriate lens for providing a spatial resolution and depth of field necessary to form a sharp focus image of substantially all of the bottom interior surface of the small container;

f) wherein the image sensor comprises sufficient pixel resolution to resolve a contaminating particle of at least 40 micrometers diameter resting on the interior bottom center of the small container;

g) wherein the image sensor will acquires images at a rate of 20 to 30 frames per second;

h) the image sensor and optical components are mounted inside a sealed enclosure with an optical window so that the image sensor can view objects outside the enclosure without obstruction;

i) the optical components are aligned so that the optical path is at a downward angle less than perpendicular from the axis of rotation permitting the sensor to view substantially all of the bottom interior surface of the small container;

j) an illumination system comprised of a cube structure with a "U" shaped channel cut into a cube of optical grade polycarbonate or acrylic so that the center of radius of the curved portion of the "U" shaped channel is aligned with the axis of rotation of the container;

k) an illumination system with the "U" shaped channel providing uniform diffuse illuminated surface large enough to allow the diameter of a small container to fit inside without interference with the walls;

l) the illumination system implements multiple light emitting diodes (LED's) arranged around three side of the diffusing cube and positioned to uniformly illuminate an cylindrical object place at the center of the "U" shape channel;

m) the illumination system utilizing one or more power supplies with control circuitry to turn on or off sections the LED's as required by the image processing system to enhance the contrast of the particles in the solution of small containers;

n) a precision drive motor is connected directly to the recessed bottom holder is used to impart rotational motion to the base of the small container with a motion processing computer and motor drive unit comprising memory for storing one or more defined motion programs;

o) the rotational motion is limited to insure that angular acceleration and velocity do not deform the meniscus to cause cavitation of the fluid or creep up the walls to the neck region of the container;

p) the rotational motion of the container imparts a motion to all particles within the fluid contents of the container;

q) the image sensor will begin to acquire images at a predefined acquisition rate after the rotational motion of the container has stopped, as images are acquired they are stored the image processing memory for analysis after the acquisition of all required images are completed, a minimum of four images are required for analysis but typically are 20 or more are used;

r) whereby the image sensor is positioned relative to the axis of rotation of the small container, whereby the focal point of detection coincides with the axis of rotation of the small container so to view the content of the solution in the small container and specifically the interior bottom of the small container with the illumination system provide a contrasting geometric shape of substantially all of the contaminating particles in the solution being identified and reporting grayscale information of each particle being displayed on a human machine interface.

2. The apparatus as claimed in claim 1, wherein the illumination cube has a clam shell design with an upper and lower shell that may be disassembled to allow access to the interior components for easy assembly and repair.

3. The apparatus as claimed in claim 1, wherein the illumination source of the illumination cube is comprised of flat panel LED's constructed with the LED's in close proximity to each to provide an extremely uniform illumination field.

4. The apparatus as claimed in claim 1, wherein the LED's utilized in the illumination cube may be energized in whole or in sections to illuminate the contents of the container being tested from various directions to provide backlighting, side lighting or a combination or both.

5. The apparatus as claimed in claim 1, wherein the diffusing element of the illumination cube is constructed of single block of optical grade polycarbonate or acrylic that is machined with an elongated "U" shaped cutout parallel to the upper and lower surfaces so that the major axis of the container is aligned with the radius of curvature of the "U" shaped cutout and thus providing illumination on all sides of the container with the exception of the viewing direction.

6. The apparatus as claimed in claim 1, wherein the sensor module is constructed with a folder optical path design through the use of mirror to extend the distance between the sensor and the container under observation to improve the depth of field while minimizing the physical separation between the sensor and the rotational axis of the container.

7. The apparatus as claimed in claim 1, wherein the sensor module may utilize one or more optical filters in the optical path between the sensor and container positioned for inspection to enhance the contrast of the contaminating particles in the solution.

8. The apparatus as claimed in claim 1, wherein the optical path of the sensor module is oriented at a downward angle relative to the axis of rotation of the container to allow substantially all of the bottom interior surface of the container to viewed by the sensor permitting the image capture of heavy contaminating particles that may be lying on the bottom surface on the container.

9. The apparatus as claimed in claim 1, wherein the optical path between the sensor and the container to be inspected and the viewing angle allow a large percentage of the fluid contents on the container to be viewed with each image acquisition and substantially the entire contents to viewed in four images.

10. The apparatus as claimed in claim 1, wherein the viewing angle of the sensor is oriented at a downward with respect to the axis of rotation with sufficient field of view allow the fluid contents of the container to be inspected from the bottom of the meniscus to the bottom interior surface.

11. The apparatus as claimed in claim 1, wherein the high density spacing of the LED's used in the illumination cube provide uniform energy of illumination so a contaminating particle produces approximately equivalent grayscale summation at all locations in the fluid volume with exception of the extreme edges of the container.

12. The apparatus as claimed in claim 1, wherein the precise control of the rotational motion of the container by the drive system is gentle and imparts motion to contaminating particles in the solution without causing violent distortion of the meniscus of cavitation within the fluid the container.

13. The apparatus as claimed in claim 1, wherein the precise rotational motion control and the ability to acquire images allows the user to study the shape of the meniscus and precisely define the parameters for a controlled particle agitation for a specific container size, shape and fluid fill level to insure reliable detection of contaminating particles.

14. The apparatus as claimed in 1, wherein the combination of illumination, sensor and precise motion control for excitation of the particle movement within the fluid of the container under inspection allows the generation of consistent grayscale images that may be compared as part of a sequence of images to identify differences between images as contaminating particles. The summation of the subtle grayscale differences can be recorded and compared with standard samples prepared with known NIST traceable particles of various sizes. A plot of grayscale summation difference versus NIST particle size will yield a calibration curve that can be used to estimate the size of an unknown particle. A separate calibration curve can be constructed for containers different shapes, sizes and fluid fill levels.

15. The apparatus as claimed in claim 14, wherein a calibration curve can be used for the rejection of unacceptable product based on size of the contaminating particle rather than the simple detection of a contaminating particle.

* * * * *